(12) United States Patent
Lieberman

(10) Patent No.: US 7,833,284 B2
(45) Date of Patent: Nov. 16, 2010

(54) ANTI-ADHESION MEMBRANE

(75) Inventor: Isador H. Lieberman, Pepper Pike, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 577 days.

(21) Appl. No.: 11/823,048

(22) Filed: Jun. 26, 2007

(65) Prior Publication Data

US 2008/0004714 A1 Jan. 3, 2008

Related U.S. Application Data

(60) Provisional application No. 60/817,250, filed on Jun. 28, 2006.

(51) Int. Cl.
*A61F 2/02* (2006.01)
(52) U.S. Cl. .................................. 623/23.74
(58) Field of Classification Search ............. 623/23.74; 604/890.1; 424/443, 445–449, 422–424, 424/433
See application file for complete search history.

(56) References Cited

U.S. PATENT DOCUMENTS

| | | | | |
|---|---|---|---|---|
| 3,710,795 A | * | 1/1973 | Higuchi et al. ............. | 424/424 |
| 3,948,254 A | * | 4/1976 | Zaffaroni .................... | 128/833 |
| 4,379,454 A | * | 4/1983 | Campbell et al. ........... | 424/448 |
| 5,057,117 A | | 10/1991 | Atweh | |
| 5,310,559 A | * | 5/1994 | Shah et al. .................. | 424/448 |
| 5,356,429 A | * | 10/1994 | Seare ............................ | 623/8 |
| 5,464,450 A | * | 11/1995 | Buscemi et al. ............. | 623/1.2 |
| 5,480,436 A | | 1/1996 | Bakker et al. | |
| 5,508,036 A | | 4/1996 | Bakker et al. | |
| 5,593,441 A | | 1/1997 | Lichtenstein et al. | |
| 5,614,284 A | * | 3/1997 | Kranzler et al. ............. | 428/138 |
| 5,634,931 A | * | 6/1997 | Kugel .......................... | 606/151 |
| 5,690,670 A | * | 11/1997 | Davidson .................... | 606/198 |
| 5,713,842 A | * | 2/1998 | Kay ............................ | 602/57 |
| 5,795,584 A | | 8/1998 | Totakura et al. | |
| 5,858,990 A | * | 1/1999 | Walsh ....................... | 514/44 R |
| 5,899,917 A | * | 5/1999 | Edwards et al. ............. | 606/195 |
| 6,031,148 A | | 2/2000 | Hayes et al. | |
| 6,080,168 A | | 6/2000 | Levin et al. | |

(Continued)

FOREIGN PATENT DOCUMENTS

WO WO-2004/010854 A2 2/2004

(Continued)

OTHER PUBLICATIONS

Product brochure from W. L. Gore for "Preclude® Vessel Guard", dated Jan. 2007.

Primary Examiner—Julian W Woo
Assistant Examiner—Son Dang
(74) Attorney, Agent, or Firm—Tarolli, Sundheim, Covell & Tummino LLP

(57) ABSTRACT

A membrane for implantation into a patient includes a first layer and a second layer. The first layer has oppositely disposed outer and inner first layer surfaces. The second layer has oppositely disposed outer and inner second layer surfaces. The second layer is at least partially attached to the first layer with the inner first and second layer surfaces adjacent one another. The inner first and second layer surfaces are resistant to biological tissue ingrowth and the outer first and second layer surfaces are conducive to biological tissue ingrowth.

18 Claims, 2 Drawing Sheets

U.S. PATENT DOCUMENTS

| | | | |
|---|---|---|---|
| 6,096,038 A * | 8/2000 | Michelson | 606/86 A |
| 6,159,142 A * | 12/2000 | Alt | 600/3 |
| 6,238,693 B1 * | 5/2001 | Luther et al. | 424/448 |
| 6,270,530 B1 * | 8/2001 | Eldridge et al. | 623/23.74 |
| 6,302,897 B1 | 10/2001 | Rousseau | |
| 6,319,264 B1 * | 11/2001 | Tormala et al. | 606/151 |
| 6,350,285 B2 * | 2/2002 | Gerlach et al. | 623/23.76 |
| 6,383,201 B1 | 5/2002 | Dong | |
| 6,416,776 B1 * | 7/2002 | Shamie | 424/423 |
| 6,726,920 B1 * | 4/2004 | Theeuwes et al. | 424/423 |
| 6,736,823 B2 | 5/2004 | Darois et al. | |
| 6,736,854 B2 | 5/2004 | Vadurro et al. | |
| 6,658,853 B2 | 7/2004 | Kieturakis et al. | |
| 6,790,213 B2 * | 9/2004 | Cherok et al. | 606/151 |
| 6,981,981 B2 | 1/2006 | Reiley et al. | |
| 2002/0001609 A1 * | 1/2002 | Calhoun et al. | 424/426 |
| 2002/0052622 A1 | 5/2002 | Rousseau | |
| 2002/0168401 A1 * | 11/2002 | Kanios et al. | 424/449 |
| 2003/0078602 A1 * | 4/2003 | Rousseau | 606/151 |
| 2003/0212426 A1 * | 11/2003 | Olson et al. | 606/191 |
| 2005/0142163 A1 * | 6/2005 | Hunter et al. | 424/423 |
| 2005/0149158 A1 * | 7/2005 | Hunter et al. | 607/119 |
| 2005/0163913 A1 * | 7/2005 | Spencer et al. | 427/2.1 |
| 2005/0177118 A1 * | 8/2005 | Hoganson et al. | 604/288.01 |
| 2005/0177249 A1 * | 8/2005 | Kladakis et al. | 623/23.74 |
| 2005/0261782 A1 * | 11/2005 | Hoganson | 623/23.74 |
| 2005/0283256 A1 | 12/2005 | Sommerich et al. | |
| 2006/0041320 A1 | 2/2006 | Matsuda | |
| 2006/0067976 A1 * | 3/2006 | Ferraro et al. | 424/426 |
| 2006/0067983 A1 * | 3/2006 | Swanick et al. | 424/434 |
| 2006/0078586 A1 * | 4/2006 | Ferraro et al. | 424/423 |
| 2006/0095134 A1 * | 5/2006 | Trieu et al. | 623/17.16 |
| 2006/0116696 A1 * | 6/2006 | Odermatt et al. | 606/151 |
| 2008/0206305 A1 * | 8/2008 | Herweck et al. | 424/423 |

FOREIGN PATENT DOCUMENTS

| | | |
|---|---|---|
| WO | WO-2006/023444 A2 | 3/2006 |

* cited by examiner

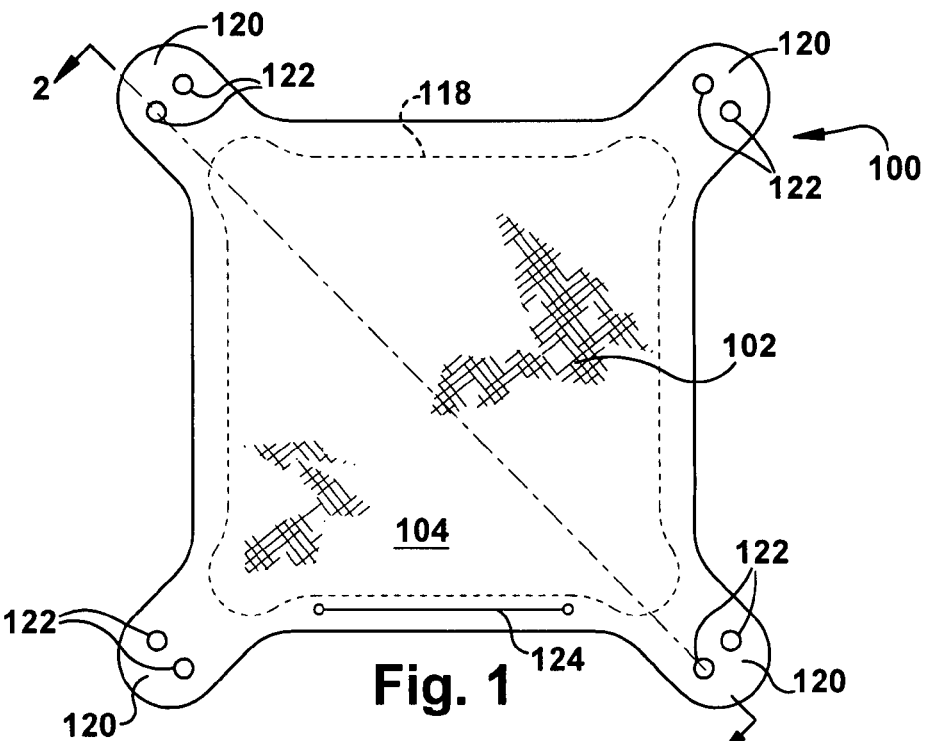
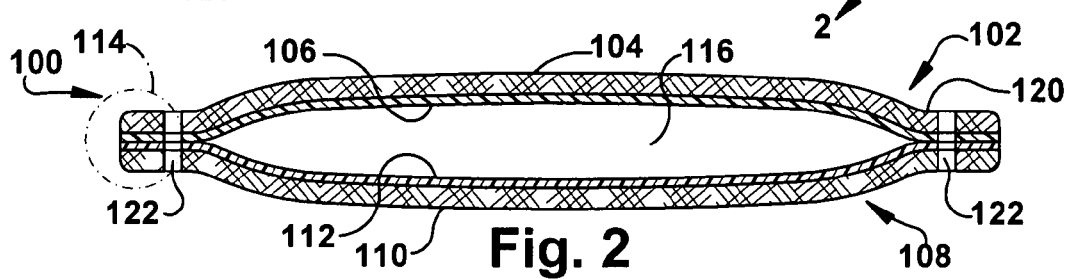
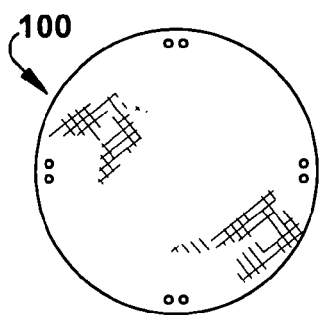
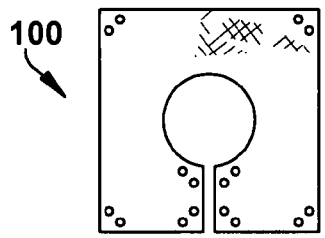
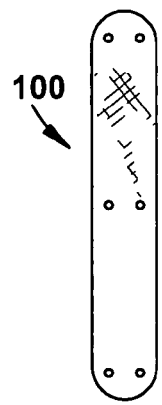
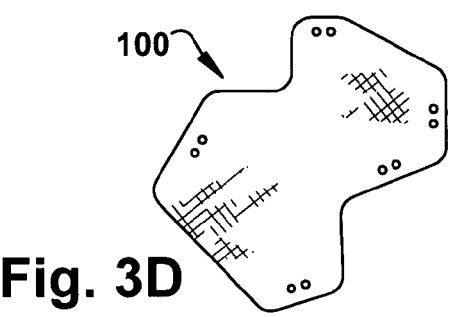

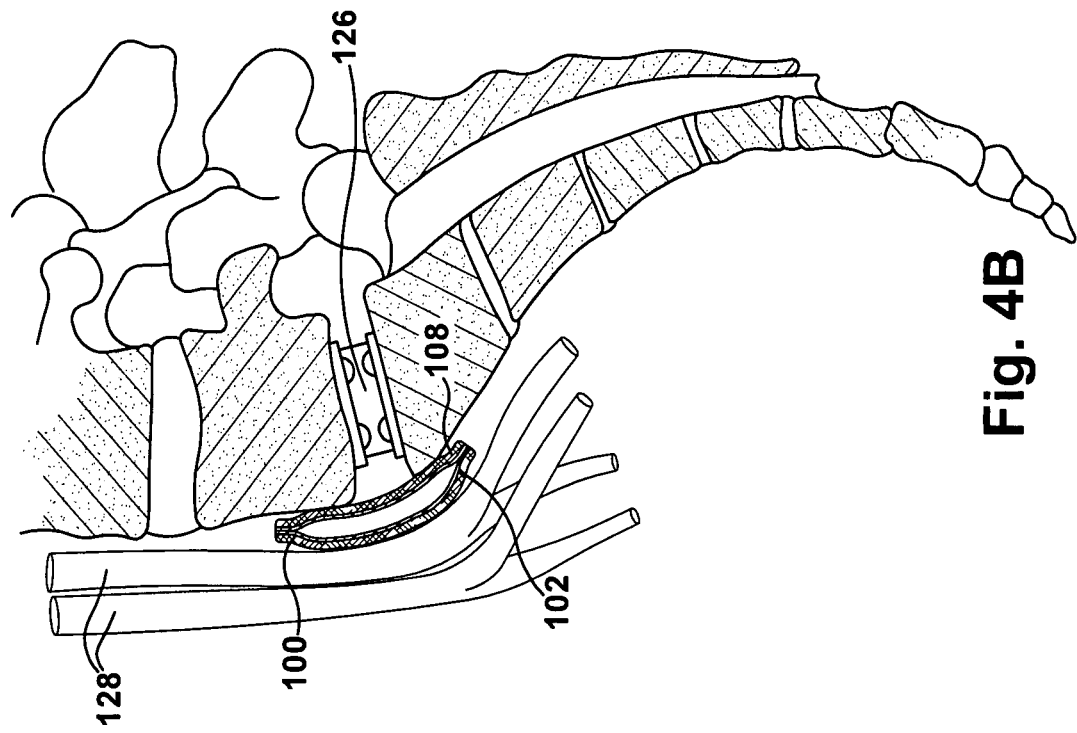
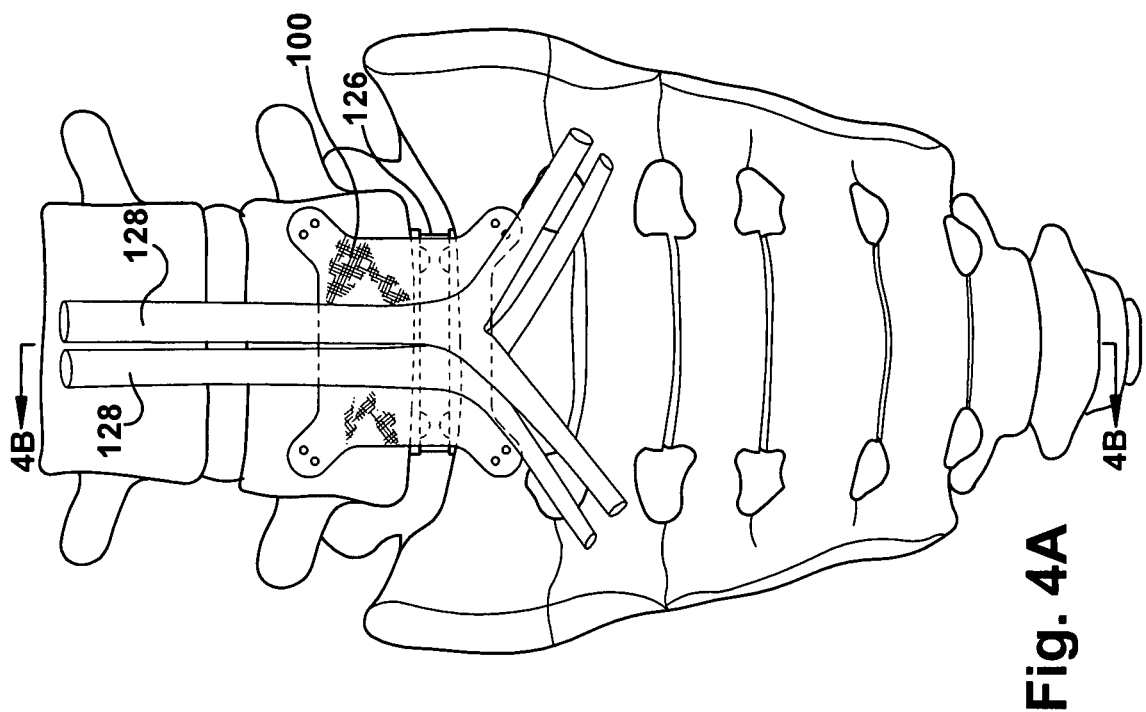
Fig. 4B
Fig. 4A

ANTI-ADHESION MEMBRANE

RELATED APPLICATION

This application claims priority from U.S. Provisional Application No. 60/817,250, filed Jun. 28, 2006, the subject matter of which is incorporated herein by reference.

TECHNICAL FIELD

The present invention relates to a membrane for implantation into a patient and, more particularly, to a membrane which resists the formation of adhesions between two structures within the patient's body.

BACKGROUND OF THE INVENTION

It is common for scar tissue to form at a surgical site within a patient's body, even after minimally invasive surgery. Depending upon the type and location of surgery, this internal scar tissue may tether adjacent blood vessels, organs, and other vital structures to the surgical bed. This can be undesirable because such tethering or adhesion may pull the vital structure out of position and/or subject the vital structure to stressing forces as the patient moves, possibly resulting in damage to the vital structure, the surgical site, or both. This undesirable adhesion is particularly pronounced when a prosthesis or other outside structure is implanted into the body. For example, adhesions tend to form between a lumbar prosthesis implant and the vena cava after anterior lumbar spine surgery, endangering the integrity of the patient's venous system.

In addition, the surgeon may desire to re-access the surgical site at a later date, for reasons including replacement of a deteriorated implant, repositioning of an implant, removal of an implant, performing a procedure at a surgical site adjacent to the previous site, and the like. Access for such revision surgery often requires that the surgeon painstakingly sever the adhesions while taking care not to damage the vital structures or the implant. Thus, adhesions can add unwanted time and complexity to what may be an already lengthy and sophisticated procedure.

One method that has been proposed to avoid the formation of adhesions between two structures of the body (hereafter discussed as being an implant and an adjacent vital structure) is to provide an anti-adhesion membrane between the structures. Such a membrane commonly is a flexible, planar sheet of material, possibly including means for attachment to an adjacent body tissue via sutures, staples, or other anchors. Current anti-adhesion membranes operate by biological inhibition of the scar response, layering of a gelatinous or other biologically compatible area to allow controlled ingrowth of adhesions in a desired area, or both. However, the known membranes may still inhibit relative movement between the implant and the vital structure. Moreover, these membranes are intended for permanent implantation and often block access to the surgical site for future revision surgery.

Accordingly, it is desirable to provide a method and apparatus of an anti-adhesion membrane which allows relative movement between an implant and an adjacent vital structure, and which facilitates access and tissue manipulation for revision surgery.

SUMMARY OF THE INVENTION

In an embodiment of the present invention, a membrane for implantation into a patient is described. The membrane includes a first layer and a second layer. The first layer has oppositely disposed outer and inner first layer surfaces. The second layer has oppositely disposed outer and inner second layer surfaces. The second layer is at least partially attached to the first layer with the inner first and second layer surfaces adjacent one another. The inner first and second layer surfaces are resistant to biological tissue ingrowth and the outer first and second layer surfaces are conducive to biological tissue ingrowth.

In an embodiment of the present invention, a membrane for implantation into a patient is described. The membrane includes a first layer and a second layer. The first layer has oppositely disposed outer and inner first layer surfaces. The second layer has oppositely disposed outer and inner second layer surfaces. The second layer is at least partially attached to the first layer with the inner first and second layer surfaces adjacent one another. A pocket edge is located between the first and second layers and defines a membrane pocket between the inner first and second layer surfaces in cooperation with the first and second layers. The membrane pocket contains a fluid.

In an embodiment of the present invention, a membrane for implantation into a patient is described. The membrane includes a first layer and a second layer. The first layer has oppositely disposed outer and inner first layer surfaces. The second layer has oppositely disposed outer and inner second layer surfaces. The second layer is at least partially attached to the first layer with the inner first and second layer surfaces adjacent one another. A pocket edge is located between the first and second layers and defines a membrane pocket between the inner first and second layer surfaces in cooperation with the first and second layers. At least one dissection line is located in at least one of the first layer, the second layer, and the pocket edge. The dissection line is adapted to selectively permit access to the membrane pocket.

BRIEF DESCRIPTION OF THE DRAWINGS

For a better understanding of the invention, reference may be made to the accompanying drawings, in which:

FIG. 1 is a plan view of one embodiment of the present invention;

FIG. 2 is a cross-sectional view taken along line 2-2 in FIG. 1;

FIGS. 3A-3D are examples of alternate configurations of the embodiment of the present invention of FIG. 1;

FIG. 4A is a plan view of the embodiment of the present invention of FIG. 1; and FIG. 4B is a cross-sectional view taken along the line 4B-4B of FIG. 4A.

DESCRIPTION OF EMBODIMENTS

In accordance with the present invention, FIGS. 1 and 2 depict a membrane 100 for implantation into a patient, according to an embodiment of the present invention. The membrane 100 allows for strategic adhesions to occur and for future access to the space between structures of the body of the patient. The membrane 100 includes a first layer 102 having oppositely disposed outer and inner first layer surfaces 104 and 106, respectively, and a second layer 108 having oppositely disposed outer and inner second layer surfaces 110 and 112, respectively.

The membrane 100 may be formed of any desired material or combination of materials, such as, but not limited to, woven, knitted, or rolled sheets of plastic, metal, fabric, biological tissue, gels, or any other suitable material for a given application of the membrane 100. The first and second layers 102 and 108 may each be planar in structure and may be as rigid or flexible as desired. The structure of the first and second layers 102 and 108 need not be homogenous throughout, and the first and second layers may have different shapes or porosities from each other. A reinforcing member (not shown) may be provided, either as a separate piece or as an integral structural feature, to one or both of the first and second layers 102 and 108, to help place and keep the membrane 100 in a desired position and orientation and to help maintain the shape of the membrane.

The first and second layers 102 and 108 are at least partially attached together with the inner first and second layer surfaces 106 and 112 adjacent one another. The attachment may be done by any suitable means, removable or permanent. For example, the first and second layers 102 and 108 may be attached by adhesive, heat sealing or melting, sutures, or the like.

Optionally, a pocket edge 114 may be located between the first and second layers 102 and 108. The pocket edge 114 may be formed by the first and second layers 102 and 108 and cooperate with the first and second layers to define a membrane pocket 116 between the inner first and second layer surfaces 106 and 112. The membrane pocket 116 could be open, as shown in FIG. 2, or could be segmented (not shown) by the first and second layers 102 and 108 being attached together at locations in addition to the pocket edge 114.

The first layer 102 could include a first layer border 118 (shown partially in dotted line in FIG. 1) at a perimeter portion thereof, and the second layer 108 could include a second layer border (not shown) at a perimeter portion thereof. The first and second layer borders 118 could extend from the same material forming the rest of the first and second layers 102 and 108, or could be specially chemically or structurally prepared areas. For instance, the first and second layer borders 118 could be thicker or more closely-woven than the rest of the first and second layers 102 and 108. When present, the first and second layer borders 118 may be adhered together to form the pocket edge 114 and may serve to reinforce the pocket edge 114 in a desired manner.

Whether or not first and second layer borders 118 are present, the membrane 100 could include an intermediate edge member (not shown) located between the first and second layers 102 and 108 and forming the pocket edge 114 in cooperation with the first and second layers. The intermediate edge member, when provided, connects the first and second layers 102 and 108, optionally in cooperation with an adhesive, suture, staple, heat weld, or other anchoring or fastening means, permanent or temporary. The intermediate edge member may be designed with a thickness such that the first and second layers are spaced apart by the intermediate edge member to provide more volume within the membrane pocket 116.

The membrane pocket 116 may contain a fluid, such as saline, gel, lubricant, gas, or any other suitable fluid. The fluid within the membrane pocket 116, when present, may act to cushion and facilitate relative movement between the first and second layers 102 and 108 in any direction. When present, the fluid may be a liquid, acting as a lubricant, or a gas, acting as a bumper. When there is fluid within the membrane pocket 116, it may be desirable for the membrane pocket to be fluidtight, and the pocket edge 114 should be configured accordingly.

Optionally, the fluid contains a therapeutic agent, such as an anticoagulant, an antibiotic, or any other desired therapeutic agent. Likewise, at least one of the inner and outer first and second layer surfaces 104, 106, 110, and 112 may be at least partially impregnated with a releasable therapeutic agent.

At least one attachment area 120 could be provided to the membrane 100 to help attach the membrane 100 to an adjacent surface, such as a body tissue of the patient or an implant. As shown in FIGS. 1 and 2, the attachment area 120 could be an attachment tab 120 formed as part of the pocket edge 114. Alternately, the attachment area 120 could be located in a portion of the membrane 100 away from the pocket edge 114, or could be a separate tab or other structural feature connected to the first and/or second layers 102 or 108. The attachment area 120 may include one or more anchor holes 122 through which a suture, staple, or other anchor may be routed to help form the desired attachment. However, when anchor holes 122 are provided, they should be located on the membrane 100 such that the membrane pocket 116 remains fluidtight. For example, the anchor holes 122 could penetrate areas of the first and second layers 102 and 108 which are adhered directly together with none of the membrane pocket 116 located therebetween, as shown in FIG. 2.

The membrane 100 could include at least one dissection line (shown partially at 124 in FIG. 1) adapted to selectively permit access to the inner first and second layer surfaces 106 and 112 from outside the membrane 100. The dissection line 124, when present, may be located in at least one of the first layer 102, the second layer 108, and the pocket edge 114. The dissection line 124 may be a thinned, scored, perforated, or otherwise structurally defined line; a printed or otherwise visually defined line, or a combination thereof. The dissection line 124 need not be a straight line, but can have any desired variable or constant contour, shape, or thickness.

The inner first and second layer surfaces 106 and 112 are optionally resistant to biological tissue ingrowth, and the outer first and second layer surfaces 104 and 110 are optionally conducive to biological tissue ingrowth. These biological traits could be provided to the surfaces 104, 106, 110, and 112 by any combination of chemical, mechanical, or other means. For example, a biological seeding coating could be provided as an outer first or second layer surface 104 or 110, or any of the surfaces 104, 106, 110, and 112 could be woven more or less tightly to encourage or discourage tissue ingrowth.

It is contemplated that the membrane 100 may include one or more positioning structures (not shown) to aid the surgeon in manipulating the membrane 100 into a desired position. For example, one or more permanent or removable tabs, loops, pockets, tool slits, or the like could be provided on any surface or edge of the membrane 100. Additionally, positioning markings or other visual or tactile indicators of orientation of the membrane 100 may be provided to assist in bringing the membrane 100 into a desired orientation at the surgical site during implantation.

The membrane 100 may take any desirable shape or configuration needed, and differently shaped or structured membranes 100 could be provided for different surgical applications. Examples of suitable membranes 100 are shown in FIGS. 3A, 3B, 3C, and 3D. In addition, one of ordinary skill in the art can readily design a membrane 100 for a desired application of the present invention.

During a surgery, the surgeon places the membrane 100 between two structures which otherwise might become adhered together by scar tissue. For example and as shown in FIGS. 4A and 4B and described below, the membrane 100 could be placed between a lumbar implant 126 and the adjacent blood vessels 128. Other examples of suitable applications for the membrane 100 include lining nerves or tendons; augmenting the pleural, pericardial, or peritoneal cavities; or even protecting organs in conjunction with transplantation.

Regardless of the application of the present invention, once the membrane 100 is placed between the two structures, the surgeon manipulates the membrane into place as desired. If attachment areas 120 are provided, the surgeon may anchor the membrane 100 into place using sutures, staples, anchors, or another fastening means in combination with the attachment areas 120. The anchor holes 122, when present, may facilitate anchoring of the membrane 100 to the adjacent blood vessels 128 or implant 126.

Once the membrane 100 is in place, as shown in FIGS. 4A and 4B, and anchored as desired, the surgeon finishes any other tasks at the surgical site and then closes the access incision to complete the surgery. As the patient recovers from the surgery, scar tissue will form adhesions between the blood vessels 128 or other body tissue and at least one of the outer first and second layer surfaces 104 and 110. For instance and as presumed in the below description, each of the first and second layers 102 and 108 may gradually adhere to one or more of the implant 126, the surrounding bone (shown in the Figures as a sacrum and vertebra), and the blood vessels 128.

Depending upon the extent of attachment between the first and second layers 102 and 108, relative sliding motion between the first and second layers may permit one or more of the implant 126, the surrounding bone, and blood vessels 128 some degree of relative movement as needed for mechanical stress relief. When a fluid in a membrane pocket 116 is present, the fluid may cushion the interface of the implant 126 and blood vessels 128. Also, at least one of the first and second layers 102 and 108 may release a therapeutic agent, when provided, to aid in healing at the surgery site or for another therapeutic purpose.

The membrane 100 may be left in place permanently if there is no reason for the surgeon to re-access the surgical site. However, when revision surgery is needed, the surgeon returns to the previous surgical site. The membrane 100 is now adhered to the adjacent blood vessels 126, and possibly the implant 126 and/or surrounding bone, by scar tissue formation. When the surgeon desires to move the implant 126 away from the blood vessels 128, or otherwise relatively move two structures separated by the membrane 100, the membrane may be dissected by the surgeon, optionally along the dissection line 124 when such is provided.

The surgeon dissects the membrane 100 by cutting into at least one of the first and second layers 102 and 108 and the pocket edge 114 and substantially separating the first and second layers 102 and 108. The inner first and second layer surfaces 106 and 112 are then exposed. The outer first and second layer surfaces 104 and 110 are each adhered to one of the implant 126 and blood vessels 128 through scar tissue ingrowth. Since the inner first and second layer surfaces 106 and 112 are resistant to biological tissue ingrowth, the membrane 100 can be split apart at the interface of the inner first and second layer surfaces 106 and 112, leaving one of the first and second layers 102 and 108 attached to each of the implant 126 and the blood vessels 128. The implant 126 and blood vessels 128 may then be separated as desired without requiring the surgeon to sever each of the adhering tethers of scar tissue individually.

Since each of the first and second layers 102 and 108 remains attached to one of the implant 126 and the blood vessels 128, these first and second layers 102 and 108 may be used to protect the associated implant or blood vessels from mechanical damage during surgery. For example, if a retractor is used, the retractor could grip the implant 126, surrounding bone, and/or blood vessels 128 at the site of the attached first or second layer 102 or 108 instead of directly contacting the implant, surrounding bone, and/or blood vessels. Therefore, the dissected membrane 100 can continue to help protect the implant 126 or blood vessels 128 from mechanical damage.

Additionally, because the first or second layer 102 or 108 is adhered to the implant 126 or blood vessels 128 with the adhesion-resistant inner first or second layer surface 106 or 112 facing outward, the dissected membrane 100 need not be removed from the implant (if the same device is re-implanted) or the blood vessels before the surgical site is closed. Instead, the first or second layer 102 or 108 will still act as a "wear pad" to prevent adhesion or mechanical damage to the associated 126 or blood vessels 128.

On the other hand, the surgeon may choose to sever the adhesions and completely remove the dissected membrane 100 from the patient. Such a procedure is relatively straightforward once the membrane 100 has been split into separate first and second layers 102 and 108, and may be facilitated by the ability of the surgeon to gradually "peel back" the first or second layer to readily access the adhesions directly below, rather than having to reach underneath a nondissected membrane 100 to access the adhesions.

Whether or not the dissected membrane 100 is removed, the surgeon may install a second membrane 100, using the above procedure, before closing the surgical site following the revision surgery. The second membrane 100 will then function as above and can be dissected as above during a second revision surgery, if needed. This cycle may be repeated as desired.

While aspects of the present invention have been particularly shown and described with reference to the preferred embodiment above, it will be understood by those of ordinary skill in the art that various additional embodiments may be contemplated without departing from the spirit and scope of the present invention. For example, the membrane 100 may be used with open or minimally invasive surgical techniques. The structures of the membrane 100 may be formed of any suitable materials, but preferably the materials are biocompatible. The first and second layers 102 and 108 could be attached together at any number of locations on the first and second layers, whether at or adjacent a perimeter of the first or second layers or spaced away from the perimeter. A third layer (not shown) could be provided and interact with one or more of the first and second layers 102 and 108 to allow for repeated dissection upon revision surgery with the same membrane 100. The surgeon could form the membrane 100 to a desired shape during surgery, the membrane 100 could be pre-fabricated, or a combination of the two could occur. The surgeon could extract fluid from within the membrane pocket 116 before dissection. The surgeon may only partially dissect the membrane 100, leaving the first and second layers 102 and 108 interconnected in a hinge-like arrangement. The membrane 100 may be dissected in an asymmetrical manner, such that a portion of each of the first and second layers 102 and 108 remains attached to one or more of the implant and vital structures. A device or method incorporating any of these features should be understood to fall under the scope of the present invention as determined based upon the claims below and any equivalents thereof.

The method and apparatus of certain embodiments of the present invention, when compared with other apparatus and methods, may have the advantages of allowing relative movement between an implant and an adjacent vital structure, and facilitating access and tissue manipulation for revision surgery. Such advantages are particularly worthy of incorporating into the design, manufacture, and operation of anti-adhesion membranes. In addition, the present invention may provide other advantages which have not yet been discovered.

Other aspects, objects, and advantages of the present invention can be obtained from a study of the drawings, the disclosure, and the appended claims.

Having described the invention, I claim:

1. A membrane for implantation into a patient, the membrane comprising:
   a first layer having oppositely disposed outer and inner first layer surfaces and including a first layer border extending from the first layer at a perimeter portion thereof;
   a second layer having oppositely disposed outer and inner second layer surfaces and including a second layer border extending from the second layer at a perimeter portion thereof, the second layer being at least partially attached to the first layer with the inner first and second layer surfaces adjacent one another; and
   a pocket edge located between the first and second layers, formed by adhesion of the first and second layer borders, and defining a membrane pocket between the inner first and second layer surfaces in cooperation with the first and second layers;
   the inner first and second layer surfaces being resistant to biological tissue ingrowth and the outer first and second layer surfaces being conducive to biological tissue ingrowth.

2. The membrane of claim 1, wherein the membrane pocket contains a fluid.

3. The membrane of claim 1, including an intermediate edge member connecting the inner first and second layer surfaces, contacting at least one of the first and second layer borders, and defining a membrane pocket between the inner first and second layer surfaces in cooperation with at least two of the first and second layers and the first and second layer borders.

4. The membrane of claim 3, wherein the membrane pocket contains a fluid.

5. The membrane of claim 1, including at least one attachment area helping to anchor the membrane to a body tissue of the patient.

6. The membrane of claim 1, wherein the membrane includes at least one dissection line adapted to selectively permit access to the inner first and second layer surfaces.

7. The membrane of claim 1, wherein at least one of the inner and outer first and second layer surfaces is at least partially impregnated with a releasable therapeutic agent.

8. The membrane of claim 1, wherein a therapeutic agent is located between the inner first and second layer surfaces.

9. A membrane for implantation into a patient, the membrane comprising:
   a first layer having oppositely disposed outer and inner first layer surfaces and including a first layer border extending from the first layer at a perimeter portion thereof, the first layer border being of different construction from the first layer;
   a second layer having oppositely disposed outer and inner second layer surfaces and including a second layer border extending from the second layer at a perimeter portion thereof, the second layer border being of different construction from the second layer, the second layer being at least partially attached to the first layer with the inner first and second layer surfaces adjacent one another;
   the inner first and second layer surfaces being resistant to biological tissue adhesion and the outer first and second layer surfaces being conducive to biological tissue adhesion; and
   a pocket edge located between the first and second layers and defining a membrane pocket between the inner first and second layer surfaces in cooperation with the first and second layers, the first and second layer borders being adhered together to form the pocket edge;
   the membrane pocket containing a fluid;
   wherein the inner first and second layer are resistant to biological tissue adhesion and the outer first and second layer surfaces are conducive to biological tissue adhesion.

10. The membrane of claim 9, including an intermediate edge member located between the first and second layers, the intermediate edge member forming the pocket edge in cooperation with at least two of the first and second layers and the first and second layer borders.

11. The membrane of claim 9, including at least one attachment area helping to anchor the membrane to a body tissue of the patient.

12. The membrane of claim 9, wherein the membrane includes at least one dissection line adapted to selectively permit access to the inner first and second layer surfaces.

13. The membrane of claim 9, wherein at least one of the inner and outer first and second layer surfaces is at least partially impregnated with a releasable therapeutic agent.

14. A membrane for implantation into a patient, the membrane comprising:
   a first layer having oppositely disposed outer and inner first layer surfaces;
   a second layer having oppositely disposed outer and inner second layer surfaces and attached to the first layer with the inner first and second layer surfaces adjacent one another;
   the inner first and second layer surfaces being resistant to biological tissue ingrowth and the outer first and second layer surfaces being conducive to biological tissue ingrowth;
   a pocket edge located between the first and second layers and defining a membrane pocket between the inner first and second layer surfaces in cooperation with the first and second layers; and
   at least one dissection line located in at least one of the first layer, the second layer, and the pocket edge, the dissection line being adapted to selectively permit access to the membrane pocket; wherein the inner first and second layer surfaces are resistant to biological tissue ingrowth and the outer first and second layer surfaces are conducive to biological tissue ingrowth.

15. The membrane of claim 14, wherein the membrane pocket contains a fluid.

16. The membrane of claim 14, wherein at least one of the inner and outer first and second layer surfaces is at least partially impregnated with a releasable therapeutic agent.

17. The membrane of claim 14, wherein the first layer includes a first layer border extending from a perimeter portion thereof, the second layer includes a second layer border extending from a perimeter portion thereof, and the first and second layer borders are adhered together to form the pocket edge.

18. The membrane of claim 17, including an intermediate edge member located between the first and second layers, the intermediate edge member forming the pocket edge in cooperation with at least two of the first and second layers and the first and second layer borders.

* * * * *